(12) United States Patent
Givois et al.

(10) Patent No.: US 6,448,240 B1
(45) Date of Patent: Sep. 10, 2002

(54) SYNERGISTIC FUNGICIDAL AND/OR BACTERICIDAL COMPOSITION

(75) Inventors: Bernadette Givois, Lyons; Marie-Pascale Latorse, Sourcieux les Mines, both of (FR)

(73) Assignee: Aventis CropScience, S.A., Lyons (FR)

( * ) Notice: Subject to any disclaimer, the term of this patent is extended or adjusted under 35 U.S.C. 154(b) by 0 days.

(21) Appl. No.: 09/555,802

(22) PCT Filed: Dec. 2, 1998

(86) PCT No.: PCT/FR98/02590

§ 371 (c)(1),
(2), (4) Date: Aug. 10, 2000

(87) PCT Pub. No.: WO99/29175

PCT Pub. Date: Jun. 17, 1999

(30) Foreign Application Priority Data

Dec. 4, 1997  (FR) .............................. 97 15585

(51) Int. Cl.⁷ ........................ A01N 57/18; A01N 43/76; A01N 59/26
(52) U.S. Cl. ........................ 514/141; 424/601; 424/602; 424/605; 424/606; 514/376
(58) Field of Search ................... 514/141, 376; 424/601, 602, 605, 606

(56) References Cited

FOREIGN PATENT DOCUMENTS

EP    0393911    10/1990

OTHER PUBLICATIONS

Tammes, *Neth. J. Plant Path.* 70, 73–80 (1964).
"Mixtures of Fungicides, Insecticides and Herbicides", *Research Disclosure*, No. 388, 489–490 (1996).
*The Pesticide Manual*, Eleventh edition, ed. C. Tomlin, British Crop Protection Council, 500–501 and 629–630 (1997).
*The Pesticide Manual*, tenth edition, ed. C. Tomlin, British Crop Protection Council, 530–532 (1994).

*Primary Examiner*—Allen J. Robinson
(74) *Attorney, Agent, or Firm*—Burns, Doane, Swecker & Mathis, L.L.P.

(57) ABSTRACT

The invention concerns a synergetic fungicide and/or bactericide composition comprising famoxadone and a phosphorous acid derivative; and a method for fighting, for cure or prevention, against phytopathogenic fungi and/or bacteria using such a composition.

10 Claims, 1 Drawing Sheet

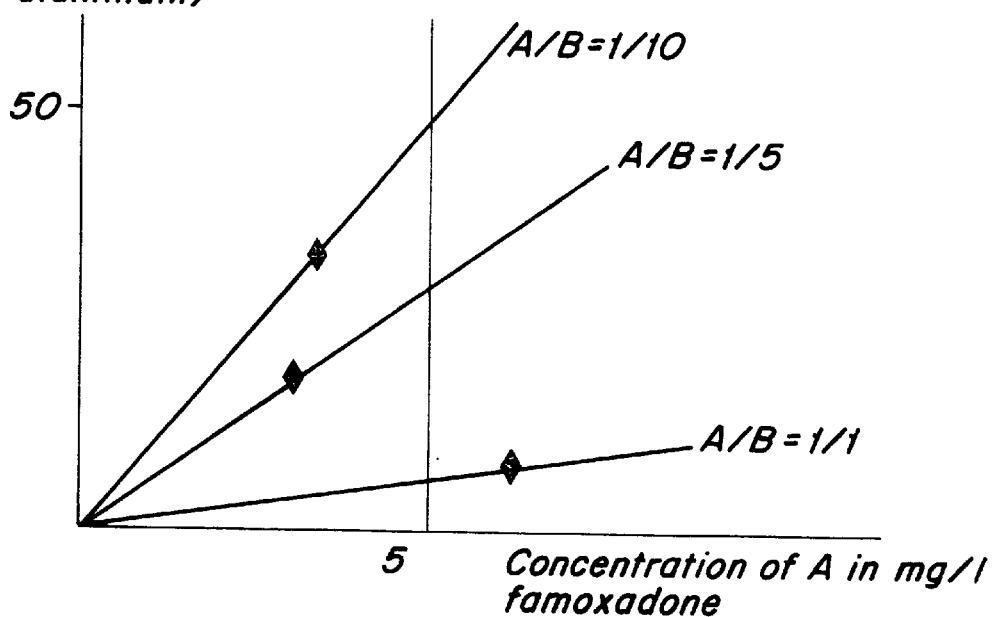

SYNERGISTIC FUNGICIDAL AND/OR BACTERICIDAL COMPOSITION

This application is a 371 of PCT/FR98/02590, filed Dec. 2, 1998.

The present invention relates to a synergistic fungicidal and/or bactericidal composition comprising famoxadone and a phosphorous acid derivative, and to a method of using this composition for the curative or preventative protection of crops against fungal attack.

It is always desirable to improve the range of activity and efficacy of such fungicidally active compounds, or to make them more potent by combining them with other molecules in order to obtain an improved product (combination with a systemic fungicide, these fungicides preferably being molecules of the "contact" type) or else to prevent the appearance of fungal strains which are resistant to these novel fungicides.

Equally, it is very desirable to have available fungicidal products which have an improved duration of action so that the number of plant protection treatments required for good control of the parasites can be spaced out over the course of time.

In any case, it is particularly advantageous to be able to reduce the quantity of chemical products sprayed in the environment while guaranteeing effective protection of the crops against fungal attack.

It has now been found that one (or more) of the above aims can be achieved by the fungicidal and/or bactericidal composition according to the present invention.

The present invention primarily therefore relates to a synergistic fungicidal and/or bactericidal composition comprising, as compound A, famoxadone, which is also known as JE874, and at least one fungicidal compound B selected from the group comprising the phosphorous acid derivatives, such as metal phosphites, such as fosetyl-aluminium, and phosphorous acid itself and its alkali metal or alkaline earth metal salts.

The fungicidal and/or bactericidal composition according to the invention advantageously comprises the components A and B in a weight ratio A/B of between 1/240 and 1/1, preferably between 1/60 and 1/7, especially advantageously in a ratio of between 1/36 and 1/12.

Naturally, this fungicidal and/or bactericidal composition can contain a single compound B or more than one such compound, for example, 1, 2 or 3 compounds B, depending on the intended use.

Amongst the more particularly preferred meanings of the above-defined compound B, fosetyl-aluminium is especially preferred. Quite unexpectedly, the composition according to the invention improves in a remarkable manner the activity of active materials taken separately for a number of fungi which are particularly harmful to crops, such as, in particular, grapevine or the potato family. This improvement manifests itself especially by a reduced dosage of each of the constituents, which is particularly advantageous for the user and the environment. The fungicidal and/or bactericidal product (mixture) thus exhibits synergistic properties which are borne out by applying the method of Tammes, "Isoboles, a graphic representation of synergism in pesticides" Netherlands Journal of Plant Pathology, 70(1964), p. 73–80.

When component B is fosetyl-aluminium, the ratio A/B is preferably between 1/60 and 1/7 this ratio especially advantageously being between 1/36 and 1/12 for all of the crops under consideration.

The structures which correspond to the common names of the active materials B are given in at least one of the 2 following works:

"The pesticide manual", edited by Clive TOMLIN, and published by the British Crop Protection Council, 10th Edition (page 530);

The "Index phytosanitaire 1994", edited by the Association de Coordination Technique Agricole, 30th Edition.

Compound A (famoxadone), itself, is a novel compound of the oxazolidinedione type which is disclosed in the European patent application published under the number EP 0393911. It is 5-methyl-5-(4-phenoxyphenyl)-3-(phenylamino-2,4-oxazolidinedione).

The fungicidal and/or bactericidal composition according to the invention comprises, as active material, a compound A and at least one compound B as a mixture with solid or liquid agriculturally acceptable carriers and/or surfactants which are also agriculturally acceptable. Substances which can be used in particular are the usual inert carriers and the usual surfactants. These compositions extend not only to compositions which are ready to be applied to the crop to be treated by means of a suitable device, such as a sprayer, but also to concentrated commercial compositions which must be diluted before being applied to the crop. By active material there is to be understood the combination of at least one compound A with at least one compound B.

These compositions can also contain any type of other ingredients such as, for example, protective colloids, adhesives, thickeners, thixotropes, penetrants, stabilizers, sequestering agents and the like. More generally, the compounds A and B can be combined with all solid or liquid additives which are conventionally used in the art of formulation.

Generally speaking, the compositions according to the invention usually contain from 0.05 to 95% (by weight) of active material, one or more liquid or solid carriers and, if appropriate, one or more surfactants.

The term "carrier" is to be understood as meaning in the present text a natural or synthetic organic or mineral material with which the active material is combined to facilitate its application to the aerial parts of the plant. This carrier is thus generally inert and must be agriculturally acceptable, especially by the treated plant. The carrier may be solid (clays, natural or synthetic silicates, silica, resins, waxes, solid fertilizers and the like) or liquid (water, alcohols, especially butanol, and the like).

The surfactant may be an ionic or nonionic emulsifier, dispersant or wetter, or a mixture of such surfactants. By way of example there may be mentioned salts of polyacrylic acids, of lignosulphonic acids, of phenolsulphonic acids or of naphthalenesulphonic acids, polycondensates of ethylene oxide and fatty alcohols or fatty acids or fatty amines, substituted phenols (especially alkylphenols or arylphenols), salts of sulphosuccinic esters, taurine derivatives (especially alkyl taurates), phosphoric esters of alcohols or of polyoxyethylated phenols, esters of fatty acids and polyols, and derivatives of the above compounds which have a sulphate, sulphonate and phosphate function. The presence of at least one surfactant is generally indispensable when the active material and/or the inert carrier are not soluble in water and when the application vehicle is water.

The compositions according to the invention for use in agriculture can therefore contain the active material within very wide limits of from 0.05% to 95% (by weight). Their surfactant content is advantageously between 5% and 40% by weight. Unless otherwise specified, the percentages given in the present description including the claims are by weight.

These compositions according to the invention, themselves, come in a wide variety of solid or liquid forms.

As solid forms of compositions there may be mentioned powders for dusting (whose active material content may be as high as 100%) and granules, especially those obtained by extrusion, by compacting, by impregnating a granulated carrier, by granulation of a powder (the active material content in these granules being between 0.5 and 80% in the last-mentioned cases), tablets or effervescent tablets.

The fungicidal and/or bactericidal composition according to the invention may also be used in the form of powders for dusting; a composition comprising 50 g of active material and 950 g of talc may also be used; a composition comprising 20 g of active material, 10 g of finely divided silica and 970 g of talc may also be used; these constituents are mixed and ground, and the mixture is applied by dusting.

As liquid forms of compositions, or forms intended to give liquid compositions upon application, there may be mentioned solutions, in particular water-soluble concentrates, emulsions, concentrated suspensions, aerosols, wettable powders (or sprayable powders), pastes, and gels.

Concentrated suspensions which can be applied by spraying are prepared in such a way that a stable fluid product is obtained which does not settle, and they usually contain 10 to 75% of active material, 0.5 to 15% of surfactants, 0.1 to 10% of thixotropes, 0 to 10% of suitable additives such as antifoams, corrosion inhibitors, stabilizers, penetrants and adhesives, and, as carrier, water or an organic liquid in which the active material is sparingly, or not, soluble: certain organic solid materials or mineral salts may be dissolved in the carrier to help prevent settling, or as antifreeze agents for the water.

By way of example there is now given a composition of a concentrated suspension:

EXAMPLE SC 1

| | |
|---|---|
| active material | 500 g |
| polyethoxylated tristyrylphenol phosphate | 50 g |
| polyethoxylated alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

Wettable powders (or sprayable powders) are usually prepared in such a way that they contain 20 to 95% of active material; they usually contain, in addition to the solid carrier, 0 to 30% of a wetter, 3 to 20% of a dispersant, and, if necessary, 0.1 to 10% of one or more stabilizers and/or other additives, such as penetrants, adhesives, anticaking agents, colorants and the like.

To obtain sprayable powders, or wettable powders, the active materials are mixed intimately with the additives in suitable mixers and the mixtures are ground in mills or other suitable grinders. This gives sprayable powders with advantageous wetting and suspending properties; they can be suspended in water to give any desired concentration, and these suspensions are very advantageously suitable for foliar application to the plants, in particular.

Instead of wettable powders, pastes may be made. The conditions and modes of making and using these pastes are similar to those for wettable powders or sprayable powders.

By way of example there are now given various compositions of wettable powders (or sprayable powders):

EXAMPLE WP 1

| | |
|---|---|
| active material | 50% |
| ethoxylated fatty alcohol (wetter) | 2.5% |
| ethoxylated phenylethylphenol (dispersant) | 5% |
| chalk (inert carrier) | 42.5% |

EXAMPLE WP 2

| | |
|---|---|
| active material | 10% |
| branched synthetic C13-oxoalcohol ethoxylated with 8 to 10 ethylene oxide units (wetter) | 0.75% |
| neutral calcium lignosulphonate (dispersant) | 12% |
| calcium carbonate (inert filler) | to 100% |

EXAMPLE WP 3

This wettable powder contains the same ingredients as in the preceding example, but in the following proportions:

| | |
|---|---|
| active material | 75% |
| wetter | 1.50% |
| dispersant | 8% |
| calcium carbonate (inert filler) | to 100% |

EXAMPLE WP 4

| | |
|---|---|
| active material | 90% |
| ethoxylated fatty alcohol (wetter) | 4% |
| ethoxylated phenylethylphenol (dispersant) | 6% |

EXAMPLE WP 5

| | |
|---|---|
| active material | 50% |
| mixture of anionic and nonionic surfactants (wetter) | 2.5% |
| sodium lignosulphonate (dispersant) | 5% |
| kaolin type clay (inert carrier) | 42.5% |

The aqueous dispersions and emulsions, for example the compositions obtained by diluting a wettable powder or an emulsifiable concentrate according to the invention with the aid of water, come within the general scope of the present invention. The emulsions may be of the water-in-oil type or the oil-in-water type and they can have a thick consistency, such as that of a "mayonnaise".

The fungicidal compositions according to the invention may be formulated in the form of water-dispersible granules, which equally come within the scope of the invention.

These dispersible granules, whose apparent density is generally between approximately 0.3 and 0.6, have a particle size of generally between approximately 150 and 2000, preferably between 300 and 1500, microns.

The active material content of these granules is generally between approximately 1% and 90%, preferably between 25% and 90%.

The remainder of these granules is essentially composed of a solid filler and, if appropriate, surface-active adjuvants which impart, to the granules, properties of dispersibility in water. These granules can essentially belong to two different types, depending on whether their filler is water-soluble or not. When the filler is soluble in water, it may be mineral or, preferably, organic. Outstanding results were obtained with urea. An insoluble filler is preferably mineral, such as, for example, kaolin or bentonite. It is advantageously accompanied by surfactants (in a proportion of 2 to 20% by weight of the granules) of which more than half is composed of, for example, at least one essentially anionic dispersant, such as an alkali metal or alkaline earth metal polynaphthalenesulphonate, or an alkali metal or alkaline earth metal lignosulphonate, the remainder being composed of nonionic or anionic wetters, such as an alkali metal or alkaline earth metal alkylnaphthalenesulphonate.

In addition, other adjuvants such as antifoams may be added, even though this is not compulsory.

The granules according to the invention can be prepared by mixing the necessary ingredients and then granulating the mixture by various techniques known per se (granulator, fluidized bed, atomizer, extrusion and the like). This generally ends with crushing followed by screening to the selected particle size within the abovementioned limits. Granules obtained as above and then impregnated with a composition which contains the active material may also be used.

It is preferably obtained by extrusion, the procedure being as indicated in the examples hereinbelow.

Example DG1: Dispersible Granules

In a mixer, 90% by weight of active material and 10% of urea beads are mixed. The mixture is subsequently ground in a pin mill. This gives a powder which is moistened with approximately 8% by weight of water. The moist powder is extruded in a perforated-roll extruder. This gives granules which are dried and then crushed and screened to give respectively only those granules which have a size of between 150 and 2000 microns.

Example DG2: Dispersible Granules

The following constituents are mixed in a mixer:

| | |
|---|---|
| active material | 75% |
| wetter (sodium alkylnaphthalenesulphonate) | 2% |
| dispersant (sodium polynaphthalenesulphonate) | 8% |
| inert water-insoluble filler (kaolin) | 15% |

This mixture is granulated in a fluidized bed in the presence of water and then dried, crushed and screened to give granules of a size between 0.15 and 0.80 mm.

These granules can be used alone, as a solution or as a dispersion in water so as to obtain the desired dose. They can also be used for preparing combinations with other active materials, especially fungicides, the latter being in the form of wettable powders or of granules or aqueous suspensions.

Those compositions which are designed to be suitable for storage and transport contain more advantageously 0.5 to 95% (by weight) of active material.

The invention furthermore relates to a method for the curative or preventative control of crop-phytopathogenic fungi and/or bacteria, characterized in that an effective, non-phytotoxic quantity of a combination of compound A and at least one compound B is applied to the aerial parts of the plants, for example in a fungicidal and/or bactericidal composition according to the invention.

The crop-phytopathogenic fungi which can be controlled by this method are especially the following:

from the group of the Oomycetes:

those of the genus Phytophthora, such as *Phytophthora phaseoli, Phytophthora citrophthora, Phytophthora capsici, Phytophthora cactorum, Phytophthora palmivora, Phytophthora cinnamoni, Phytophthora megasperma, Phytophthora parasitica, Phytophthora fragariae, Phytophthora cryptogea, Phytophthora porri, Phytophthora nicotianae, Phytophthora infestans* (solanum blight, especially potato or tomato blight);

from the family of the Peronosporaceae, in particular *Plasmopara viticola* (grapevine downy mildew), *Plasmopara halstedei* (sunflower downy mildew), Pseudoperonospora sp. (in particular cucurbit downy mildew (*Pseudoperonospora cubensis*) and hop downy mildew (*Pseudopernospora humuli*)), *Bremia lactucae* (lettuce downy mildew), *Peronospora tabacinae* (tobacco blue mould), *Peronospora destructor* (onion downy mildew), *Peronospora parasitica* (brassica downy mildew), *Peronospora farinosa* (endive mildew and beet mildew), from the group of the Adelomycetes:

those of the genus Alternaria, for example *Alternaria solani* (solanum early blight, especially tomato and potato early blight), those of the genus Guignardia, especially *Guignardia bidwellii* (grape black rot), those of the genus Venturia, for example *Venturia inaequalis, Venturia pirina* (apple or pear scab), those of the genus Taphrina, for example *Taphrina deformans* (peach leaf curl).

Diseases of bacterial origin which can be controlled by this method are in particular fire blight, *erwinia amylovora;* bacterial spot of stone fruits, *xanthomonas campestris;* pear bacterial canker, *pseudomonas syringae.*

The crops under consideration for the purposes of the present invention are preferably vegetable crops (beans, onions, cucurbits, cabbage, potatoes, tomatoes, capsicums, spinach, peas, lettuce, celery, endives), fruit crops (strawberry plants, raspberry plants), arboricultural crops (apple trees, pear trees, cherry trees, ginseng, lemon trees, coconut palms, pecan trees, cacao trees, nut trees, hevea trees, olive trees, poplars, banana plants), grapevines, sunflowers, beet, tobacco and ornamentals.

A classification neither by fungi nor by bacteria aimed at, but by target crops, can be illustrated as below:

grapevine: oidium (*Uncinula necator*), downy mildew (*Plasmopara viticola*), excoriosis (*Phomopsis viticola*) and black rot (*Guignardia bidwellii*), vegetable crops: downy mildews (Peronospora sp., *Bremia lactucae*, Pseudoperonospora sp.), arboriculture: scab (*Venturia inaequalis, V. pirina*), bacterial diseases (*erwinia amylovora, xanthomonas campestris, pseudomonas syringae*), citrus fruit: scab (*Elsinoe fawcetti*), melanose (*Phomopsis citri*) and diseases caused by Phytophthora sp.

The fungicidal and/or bactericidal composition of the invention is applied by means of various treatment methods, such as:
    spraying a liquid comprising said composition onto the aerial parts of the crops to be treated,
    dusting, incorporation of granules or powders into the soil, pouring, injection into trees, or painting on.

The preferred treatment method is spraying a liquid onto the aerial parts of the crops to be treated.

"Effective, non-phytotoxic quantity" is to be understood as meaning such an amount of composition according to the invention to allow fungi and bacteria which are present or likely to appear on the crops to be controlled or destroyed while avoiding any notable symptoms of phytotoxicity on said crops. Such a quantity is likely to vary within wide limits, depending on the fungus or the bacterium to be controlled, the type of crop, the climatic conditions, and the compounds in the fungicidal and/or bactericidal composition according to the invention. This quantity can be determined by systematic field trials known to the skilled worker.

When making use of the method according to the invention, the use concentrations for grapevines, vegetable crops, arboriculture, citrus fruit and the like will generally be:
    for foliar treatment:
        500 to 6000 g/ha of compound B, for example fosetyl-aluminium, +25 to 500 g/ha of compound A, more precisely 1000 to 3000 g/ha+50 to 150 g/ha, that is to say a total dose of composition according to the invention of between 525 and 6500 g/ha, preferably between 1050 and 3150 g/ha. 1200 to 1800 g/ha of compound B and 50 to 100 g/ha of compound A are preferably used, that is to say a total dose of composition according to the invention of between 1250 g/ha and 1900 g/ha.

Finally, the invention relates to a product comprising at least one compound A and at least one compound B for controlling phytopathogenic fungi and/or bacteria in an environment by simultaneous, sequential or separate application.

The example which follows is given purely by way of illustrating the invention which is limited thereby in no way whatsoever.

In the figure appended to the present text, the dose of each active material taken in isolation which is required for controlling the phytopathogenic fungus at the level indicated is compared with that of 2 active materials as a mixture. The effective dose of each active material taken in isolation is indicated on the abscissa and on the ordinate, and a straight line is drawn which intersects these 2 axes and connects these 2 doses. When an active material taken in isolation is not efficient, the straight line is parallel with the axis of the coordinates indicating the doses of this active material. As regards the two active materials as a mixture, the dose of the mixture at a given ratio is indicated by a point.

Example 1: In-vivo test of the combination of famoxadone and fosetyl-aluminium on *Plasmopara viticola* (grapevine downy mildew) by preventative treatment 5 days before inoculation.

Dispersible granules of 50% compound A (famoxadone) and dispersible granules of 80% compound B (fosetyl-aluminium) are used. Dilute suspensions are prepared from these compositions by diluting them with water, and the two liquids are mixed in such a way that different ratios of the two products famoxadone and fosetyl are obtained. The A/B ratios studied were selected between 1/10 and 1/1, that is to say equalling 0.1–0.2 and 1.

Grapevine cuttings (*Vitis vinifera*), cv. Chardonnay are grown in pots. When these plants are 2 months old (8- to 10-leaf stage, height 10 to 15 cm), they are treated by being sprayed with the suspension above.

Plants used as controls are treated with a similar suspension which, however, does not contain active material ("zero-formulation").

After 5 days, during which the plants are kept at 20° C. and a relative humidity of 70%, each plant is inoculated by being sprayed with an aqueous suspension of *Plasmopara viticola* spores obtained from sporulated leaves which had been inoculated 7 days earlier. These spores are suspended at 100,000 units per $cm^3$ of inoculum. Inoculation is performed by spraying the underside of the leaves with the inoculum.

The inoculated plants are then incubated for seven days at 20–22° C. and a relative humidity of 90–100% under natural light.

The test is evaluated 7 days after inoculation by comparing the plants with the control plants. In Table 1, we have chosen to present, as numbers, the results which correspond to ED70 and 90% (effective doses which have a 70 or 90%, respectively, control effect on the disease) for the different ratios of mixtures studied, calculated on the basis of 3 replications per factor.

TABLE 1

| 5-day-preventative application on downy mildew of grapevines. Fosetyl (C) alone is inactive at all doses studied (ED90 > 2000 mg/l) | | |
|---|---|---|
|  | ED70 | ED90 |
| A = famoxadone | 2 | 5.5 |
| B = fosetyl - aluminium | >2000 | >2000 |
| A/(B) = 1/10 | 1.5 | 3.6 |
| A/(B) = 1/5 | 1.5 | 3.1 |
| A/(B) = 1/1 | 2 | 6.3 |

Illustration in the form of a TAMMES graph is only shown for ED90. The results obtained are shown in the form of points which correspond to 90% destruction of the parasite and arranged in a Tammes isobole diagram which shows, on the abscissa, the doses of A expressed in ppm (mg/l) and, on the ordinate, the doses of B, also in ppm (mg/l) (cf. FIG. 1/1).

The diagram in FIG. 1 is obtained. It can clearly be seen that, when fosetyl is added to famoxadone at a ratio of 1/10 and 1/5, the dose of famoxadone required to control the mildew for a 5-day-preventative treatment is lowered to under 5.5 mg/l, which corresponds to the famoxadone—only dose which must be applied to obtain 90% control of the disease.

The location of the points obtained indicates a unilateral effect which is qualified as a "one-sided effect" according to the method of TAMMES. This location corresponds to a type II isobole according to this method (TAMMES P.M.L. (1964) Isoboles, a graphic representation of synergism in pesticides; *Netherlands Journal of Plant Pathology* 70, 73–80). The location of points corresponding to A/(B) ratios of 1/10 and 1/5 signifies that the products are potentially synergistic. In the case of the ratio 1/1, there is an additive effect of the two-component mixture compared with the products alone.

When the famoxadone concentration in the mixture is lower than the fosetyl-aluminium concentration by a factor of 5 or 10, the two products are guaranteed to be compatible (additive behaviour) and potentially synergistic.

What is claimed is:

1. A fungicidal composition comprising, synergistic fungicidally effective amounts of (A) famoxadone and (B) at least one fungicidal compound selected from the group consisting of metal phosphites, phosphorous acid and alkali metal and alkaline earth metal salts of phosphorous acid;

the components A and B being present in the composition in a weight ratio A/B of between 1/240 and 1/1.

2. A fungicidal composition according to claim 1, wherein compound B is fosetyl-aluminium.

3. A fungicidal composition according to claim 1, wherein the ratio A/B is between 1/60 and 1/7.

4. A fungicidal composition according to claim 1, wherein compounds A and B are admixed with solid or liquid agriculturally acceptable carriers and/or surfactants.

5. A fungicidal composition according to claim 1, which comprises from 0.05 to 95% by weight of active material.

6. Method for the control of phytopathogenic fungi in an environment, wherein a composition according to claim 1 is applied to said environment, the composition being in an overall quantity which is effective and non-phytotoxic.

7. Method for the curative or preventative control of crop-phytopathogenic fungi wherein an effective, non-phytotoxic quantity of a fungicidal composition according to claim 1 is applied to the aerial parts of plants.

8. Method according to claim 7, wherein the aerial parts of crops to be treated are sprayed with a liquid comprising the fungicidal composition according to claim 1.

9. Method for the control of crop-phytopathogenic fungi according to claim 8, wherein a total dose of composition of between 525 and 6500 g/ha is applied.

10. Method according to claim 9, wherein a total dose of composition of between 1250 and 1900 g/ha is applied.

* * * * *